United States Patent [19]

Mangus

[11] Patent Number: 5,016,401
[45] Date of Patent: * May 21, 1991

[54] CAUTERY TIP CLEANER AND HOLDER

[76] Inventor: Donald J. Mangus, 500 Cohasset Rd., Ste. 27, Chico, Calif. 95926

[*] Notice: The portion of the term of this patent subsequent to Mar. 5, 2008 has been disclaimed.

[21] Appl. No.: 487,614

[22] Filed: Mar. 2, 1990

Related U.S. Application Data

[63] Continuation-in-part of Ser. No. 247,763, Sep. 21, 1988.

[51] Int. Cl.$^5$ .............. B24B 1/00; B24D 11/00; A47L 17/08; A47L 25/00
[52] U.S. Cl. .................... 51/328; 51/394; 51/395; 51/401; 15/218.1; 15/244.1
[58] Field of Search .......... 51/16, 17, 181 R, 401, 51/354, 358, 391, 404, 285, 328, 394, 395, 401; 15/218.1, 118, 244, 209 B, 209 C, 210 B, 244.1; 606/37, 39, 40, 45, 49

[56] References Cited

U.S. PATENT DOCUMENTS

| | | | |
|---|---|---|---|
| Re. 29,678 | 6/1978 | Antonini et al. | 206/571 |
| 1,652,875 | 12/1927 | Rein et al. | 15/210.13 |
| 2,699,565 | 1/1955 | Brough | 15/236 |
| 3,094,730 | 6/1963 | Schwarz | 15/210 |
| 3,862,522 | 1/1975 | Mednick | 51/404 X |
| 3,982,357 | 9/1976 | Eldridge | 51/181 R |
| 3,998,012 | 12/1976 | Ness | 51/391 |
| 4,011,693 | 3/1977 | Eldridge, Jr. et al. | 51/354 |
| 4,103,388 | 8/1978 | DeVitis | 15/210 B |
| 4,164,054 | 8/1979 | Hanson et al. | 15/210 B |
| 4,361,926 | 12/1982 | Brush et al. | 15/236 R |
| 4,506,404 | 3/1985 | Clay | 15/244 |
| 4,543,751 | 10/1985 | Alikhan | 51/181 R |
| 4,547,923 | 10/1985 | DeVries et al. | 15/104 |
| 4,704,760 | 11/1987 | Grieshaber | 415/218.1 |

*Primary Examiner*—Frederick R. Schmidt
*Assistant Examiner*—Bruce P. Watson
*Attorney, Agent, or Firm*—Virginia S. Medlen

[57] ABSTRACT

An inexpensive, lightweight apparatus and method is provided for removing coagulum and other debris from the tip of cautery blades and needles during use and for holding cautery blades and needles when not in use. The cleaner comprises a pad having a lower compressible portion and an upper fibrous abrasive portion which is mounted to a hard, non-compressible base. The apparatus can be attached to a surgical drape or other accessible surface to permit cleaning using only one hand to manipulate the cauterizing instrument. Cautery tips and other sharp surgical instruments are cleaned by plunging them into, and then withdrawing them from, the abrasive pad. The pad also provides a convenient structure for holding cautery tips and other sharp surgical instrument in a point down, base up configuration when the instruments are not in use.

12 Claims, 2 Drawing Sheets

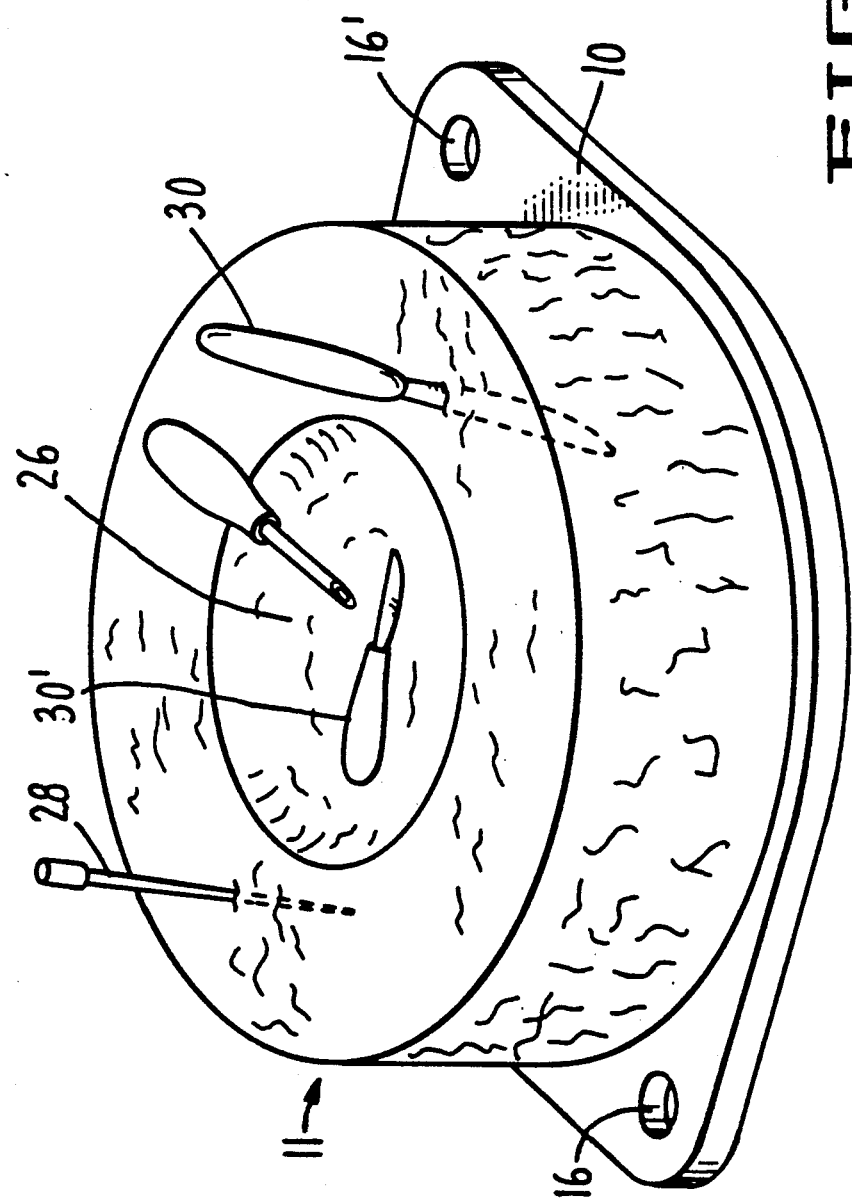

CAUTERY TIP CLEANER AND HOLDER

RELATED APPLICATION DATA

This application is a continuation-in-part of commonly owned and copending U.S. patent application Ser. No. 247,763 filed 9/21/88.

TECHNICAL FIELD

The present invention relates to medical devices. In particular, the present invention relates to a device for cleaning and holding cauterizing instrument tips during surgery.

BACKGROUND ART

Cauterizing instruments are commonly used in surgery for making and cauterizing incisions and wounds. Such cauterizing instruments are typically used with a flat blade tip or a needle tip, depending upon the extent of cauterizing required. Such flat blade tips and needle tips are available in varying sizes.

As such cauterizing instruments are used, coagulated blood, small bits of flesh and other debris adhere to the tip, causing a degradation in the current flow and efficiency of the cauterizing process, and obstructing the surgeon's view of the tip of the instrument. Thus, it is necessary to periodically remove the coagulum and debris from the tip during use of the cauterizing instrument.

Coagulum and debris can be removed from a cautery tip by wiping the tip repeatedly on a piece of sandpaper which is taped or pinned within reach of the surgeon, typically on the patient's surgical drape. This method usually requires that the surgeon twist or rotate his wrist as he cleans the cauterizing instrument to insure that all surfaces of the cautery tip are sufficiently cleaned. This method is disadvantageous because it is time consuming and takes the attention of the surgeon away from the patient and directs it to the cleaning process. Further, with sandpaper alone there may be a danger of accidental needle sticks to the patient if the sandpaper is accidentally perforated during the cleaning process.

Other, more complex devices for cleaning cautery tips are also found in the art. For example, U.S. Pat. No. 4,506,404 provides a disposable sponge for cleaning surgical instruments. U.S. Pat. No. 4,361,926 to Brush provides a cautery tip cleaner which is attached to the cauterizing instrument for moving over the cautery tip for removing the coagulum. However, these devices are disadvantageous because they require two-handed operation and take the attention of the surgeon away from the patient.

One-handed devices for cleaning cautery tips are also known. For example, U.S. Pat. Nos. 4,011,693 and 3,982,357 disclose cautery tip cleaners having confronting abrasive strips urged into mutual engagement by magnetic force. Flat cautery tips are cleaned by drawing them between the confronting abrasive strips. U.S. Pat. No. 4,547,923 discloses a compressed coil spring in which a flat cautery blade is cleaned by drawing it through two adjacent individual coils. The problem with these devices is that they are relatively complex and correspondingly expensive to produce, and they do not provide an efficient means for cleaning cautery needles.

Furthermore, none of the devices known to applicant provide both a structure capable of cleaning cautery tips and holding them when they are not in use.

Therefore, the need exists for a simple and inexpensive apparatus for efficiently and quickly cleaning both cautery needles and blades by a one-handed operation, for holding cautery needles and blades (and other surgical instruments as well) when they are not in use, and in which the possibility of accidental needle sticks to the patient or to medical personnel is substantially reduced or eliminated.

SUMMARY OF THE INVENTION

The present invention provides a lightweight, simple, inexpensive cautery tip cleaner and holder which efficiently and quickly cleans both cautery needles and cautery blades by a one handed operation.

In one embodiment, the present invention provides a compressible pad having a thick, fibrous abrasive portion on top and a hard base attached to the bottom. The fibrous abrasive portion contains one or more elongated cuts or slits for cleaning cautery blades, with the cuts partially penetrating the fibrous abrasive portion to a depth which is less than the thickness of the abrasive portion to form two opposing abrasive walls and an abrasive floor. Cautery blades are cleaned by pressing them down between opposing abrasive walls and against the abrasive floor, drawing them through the elongated cuts in the surface of the compressible pad. Cautery needles are cleaned by plunging them through the fibrous abrasive portion. The cautery tip cleaner can be attached to a surgical drape or other surface within easy reach of the surgeon by means of an adhesive strip or patch attached to the underside of the hard base.

In another embodiment, the present invention provides a pad of fibrous, abrasive material mounted on a compressible sponge pad of similar size and shape which is mounted on a hard base. The fibrous abrasive pad contains one or more elongated cuts along its top surface which penetrate the surface without penetrating through the bottom of the fibrous abrasive pad.

In yet another embodiment, the present invention provides a thick, fibrous abrasive pad attached to a hard base. The fibrous pad is of sufficient thickness and size to hold a plurality of cautery tips or other sharp surgical instruments in a point down and base up configuration when such instruments are not in use. The fibrous pad may have a recess in the center for holding other surgical instruments before or after use. Sharp cautery tips or other surgical instruments are cleaned by plunging them into the fibrous pad and withdrawing them from the fibrous pad.

In all embodiments the compressible, fibrous pad is attached to a hard base for preventing accidental needle punctures. The hard base can be attached to a surgical drape or other surface within easy reach of the surgeon by means of an adhesive strip or patch attached to the underside of the hard base or by providing a hard base with holes for using fasteners.

Other embodiments and modifications will become apparent from the detailed description set forth below.

BRIEF DESCRIPTION OF THE DRAWINGS

A better understanding of the invention and its advantages will be apparent from the detailed description taken in conjunction with the accompanying drawings in which.

DETAILED DESCRIPTION

Figure 1:
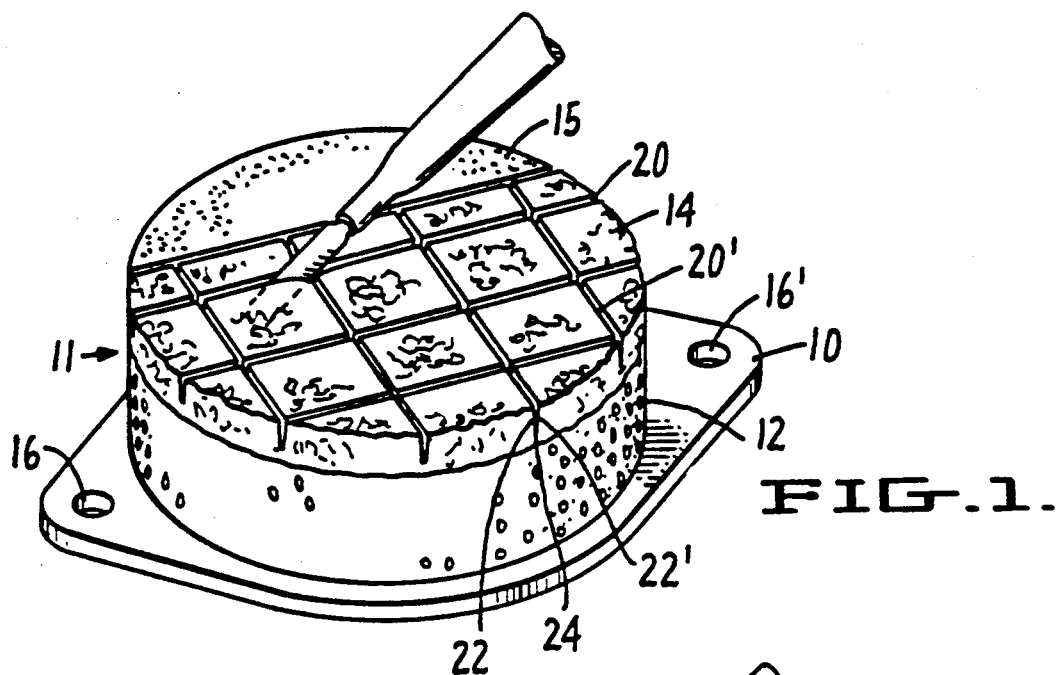
FIG. 1 is a perspective top external view of a cautery tip cleaner of the present invention.
Figure 2:
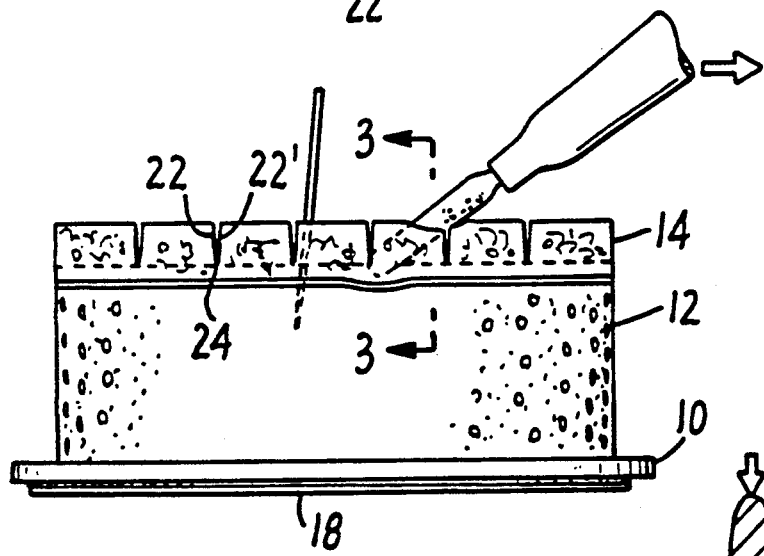
FIG. 2 is a side view of a cautery tip cleaner of the present invention.

FIGS. 1 and 2 show a cautery tip cleaner of the present invention. The cautery tip cleaner comprises a base 10 on which is mounted a pad 11 having a compressible portion 12 and a fibrous, abrasive portion 14.

Base 10 is preferably constructed from a hard, generally noncompressible material such as hard plastic or metal. Base 10 is most preferably resistant to penetration by cautery needles. Base 10 can also be adapted for mounting the cautery tip cleaner to a surface within easy reach of a surgeon or other user, such as a surgical drape, by providing an adhesive strip or patch 18 on the bottom of the base 10 for attaching the cautery tip cleaner to the surface. In addition, or in lieu of the adhesive 18, holes 16, 16' may be provided in the base for pinning the cautery tip cleaner to the surgical drape.

Abrasive portion 14 is constructed from a fibrous abrasive material such as 3M's SCOTCHBRITE® cleaning and polishing material. Abrasive portion 14 is provided with one or more elongated cuts 20, 20' which penetrate the surface of the abrasive portion to a depth sufficient to permit the cleaning of the tip of the cautery blade without exceeding the thickness of the abrasive portion. Thus, the fibrous abrasive portion should be sufficiently thick to provide in each elongated cut 20, 20' opposing abrasive surfaces 22, 22' for cleaning the sides of a cautery blade and an abrasive floor 24 for cleaning the edge of a cautery blade. Optionally, a portion of the top surface of abrasive portion 14 can include coarse sandpaper 15 for removing the most resistant coagulum from the cautery tip.

Compressible portion 12 is preferably constructed from sponge, or other similar elastically compressible material. In this embodiment pad 11 is formed by attaching a pad of fibrous abrasive material of the desired thickness on top of a similarly sized pad of sponge. Attachment can be made using any suitable adhesive Alternatively, compressible portion 12 may consist of an additional thickness of fibrous abrasive material underlying abrasive portion 14. Such a pad can be constructed from a single thickness or piece of fibrous, abrasive material divided into an upper portion or zone for cleaning and a lower portion or zone for providing compression if the fibrous, abrasive material is sufficiently elastically compressible so that the downward pressure of the cautery blade on the floor 24 of an elongated cut 20 in the upper portion will compress the underlying fibrous material in the lower portion against the hard base 10, deforming the floor 24 and drawing the opposing abrasive surfaces 22, 22' down and against each side of the cautery blade. Further, by making the pad from one piece of fibrous, abrasive material the production costs involved in assembling the cautery tip cleaner should be reduced.

Pad 11 is preferably from about 1.25 to about 1.5 inches thick. The length and width (or diameter) of the pad 11 will vary depending upon the use. This size makes it easy for the user to clean cautery tips quickly with minimal distraction from the operating field. Although the general shape of the pad 11 is shown as being round, one skilled in the art will recognize that many different shapes can be used including oval, rectangular, pyramidal, and polygonal.

Figure 3:
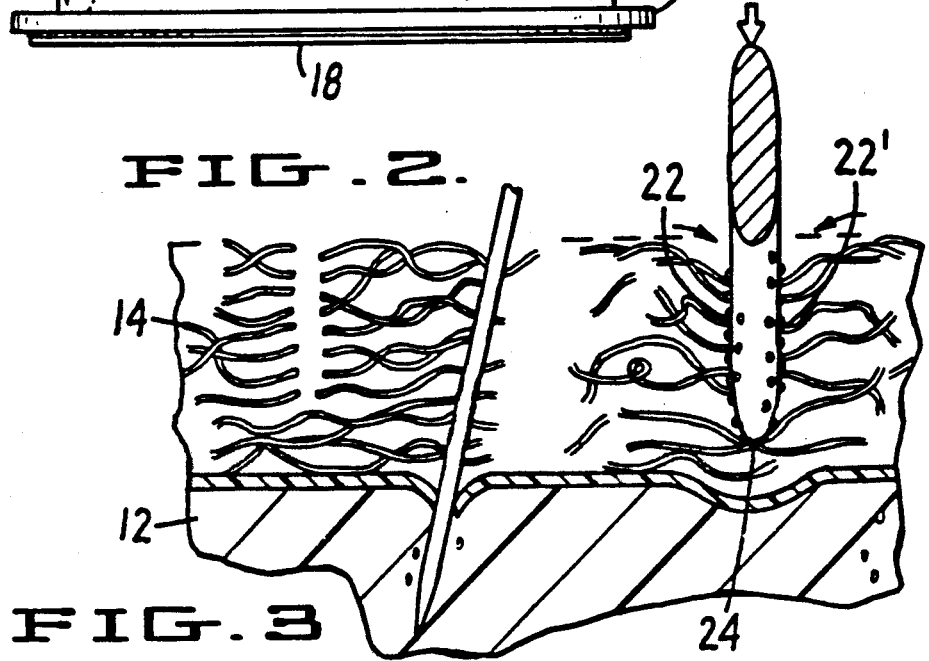
FIG. 3 is a sectional side view of a cautery tip cleaner of the present invention taken along line 3—3 of FIG. 2; and, FIG. 4 is a perspective top external view of a cautery tip cleaner and holder of the present invention.

As shown additionally in FIG. 3, to clean a cautery blade, the blade is pressed down into an elongated cut 20 and drawn through the cut 20 towards the other end of the elongated cut 20. As the flat edge of the blade is pressed against floor 24, the underlying material compresses against the hard base 10 and the floor 24 deforms, drawing the opposing abrasive surfaces 22, 22' down and together against the sides of the blade. The dual motion of downward compression and lateral movement through the elongated cut 20 efficiently and quickly removes coagulum and debris from a cautery blade and can be easily accomplished using only one hand.

To clean a cautery needle, the user simply plunges the needle through the abrasive portion 14 and then retracts it. Because the abrasive portion 14 is a fibrous abrasive which surrounds and scours off all sides of the needle as the needle penetrates the abrasive portion 14, no rotation of the needle is required; therefore the surgeon need not rotate or twist his wrist during the cleaning process. In the preferred embodiment, where compressible portion 12 is constructed from sponge, the scouring action of the abrasive portion 14 is supplemented by the wiping action of the compressible portion 12. Because the compressible portion 12 is mounted on a hard base 10, there is no danger of a needle accidentally penetrating the compressible portion 12 and puncturing the patient.

FIG. 4 shows a cautery tip cleaner and holder of the present invention in which pad 11 is comprised of fibrous, abrasive material mounted on hard base 10. In this embodiment, pad 11 is preferably at least about 1.5 inches thick and of a large enough size to hold a plurality of sharp cautery tips or other surgical instruments 28, 30 point down and base up when they are plunged into the fibrous abrasive pad 11. For example, a pad 11 of ten or twelve inches in diameter would be sufficient to hold many cautery tips or other sharp instruments point down. The act of plunging these instruments into the pad for holding, and the later withdrawal of the instruments, also serves to clean them. Pad 11 may optionally contain a shallow, bowl-like depression 26 to provide a safe place for holding cautery tips or other surgical instruments 30' which cannot be plunged into pad 11 before or after use.

In this embodiment, as well as in the other embodiments disclosed above, accidental needle sticks or cuts from other sharp instruments can be drastically reduced or eliminated altogether by providing a safe zone for cleaning and holding sharp instruments point down. With the appearance of Acquired Immuno Deficiency Syndrome (AIDS), and the possibility of transmitting other blood-borne diseases, the prevention of accidental sticks or cuts has become of increasing concern to medical personnel. The instant invention is designed to help alleviate that concern by providing a device having a puncture resistant base for cleaning and holding the sharp instruments in the safest configuration, with the point down.

One skilled in the art will recognize at once that it would be possible to construct the various components of the present invention from a variety of materials which are sterilizable. The present invention can be constructed so that it is either reusable or disposable after a first use. While the preferred embodiment and alternative variations have been described in detail and shown in the accompanying drawings, it will be evident that other and various further modifications are possible without departing from the scope of the invention as embodied in the claims.

I claim:

1. A method for cleaning surgical cautery tips using a cautery tip cleaner comprising a relatively thick sterilizable, compressible pad mounted on a substantially non-compressible, puncture resistant base having a means for attaching the cautery tip cleaner to a surface within easy reach of a user, said compressible pad including a upper fibrous abrasive portion having a top surface, said upper fibrous abrasive portion being sufficiently thick so that if a cautery tip is pushed into said abrasive portion and withdrawn, any coagulum or debris attached to said tip will be substantially removed by the fibrous abrasive material, said method comprising:
   attaching the cautery tip cleaner to a surface within easy reach of a user;
   pushing the point of the cautery tip through the top surface of the upper fibrous abrasive portion and well into the compressible pad of the cautery tip cleaner; and,
   withdrawing the cautery tip from the compressible pad of the cautery tip cleaner.

2. A surgical cautery tip cleaner and holder for cleaning surgical cautery tips and other sharp surgical instruments and for holding cautery tips and other surgical instruments in a point down, base up configuration comprising:
   a hard base having a bottom surface and a top surface, said base being resistant to penetration by needles or other sharp objects;
   a relatively thick compressible pad mounted on the top surface of the hard base and having an upper fibrous abrasive portion and a lower compressible portion, said upper abrasive portion having a top surface and sufficient thickness to clean a cautery tip when the point of the cautery tip is plunged from the top surface well into the pad and withdrawn, said compressible pad having sufficient thickness to support a plurality of cautery tips in a point down, base up configuration when such tips are plunged into the pad and released;
   said base and said compressible pad being constructed from materials suitable for sterilizing.

3. The cautery tip cleaner and holder of claim 2 additionally comprising a means for attaching the base to a surface within easy reach of a user.

4. The cautery tip cleaner and holder of claim 3 in which said means for attaching the base to a surface comprises adhesive attached to the bottom surface of the hard base.

5. The cautery tip cleaner and holder of claim 2 in which said compressible pad also contains a depression for holding surgical instruments in a generally horizontal orientation when not in use.

6. The cautery tip cleaner and holder of claim 2 in which the upper fibrous abrasive portion and lower compressible portion of the compressible pad are both comprised of fibrous, abrasive material.

7. The cautery tip cleaner and holder of claim 2 in which said upper fibrous abrasive portion additionally contains one or more elongated slits which penetrate the surface of the upper fibrous abrasive portion and which have a first end, a second end, opposing abrasive walls and an abrasive floor for cleaning a cautery blade having two sides and an edge by pressing the edge of the blade down between any two opposing abrasive walls at the first end deforming the floor and compressing the lower compressible portion to bring the opposing abrasive walls together against the sides of the cautery blade and then drawing the blade through the slit towards the second end to clean the cautery blade.

8. An apparatus for cleaning and holding surgical cautery tips comprising:
   a substantially non-compressible base having a top surface and a bottom surface, said base being resistant to penetration by sharp surgical instruments;
   a means for attaching said base to a surface within easy reach of a user;
   a relatively thick, fibrous abrasive pad mounted on the top surface of the base, said pad having a top surface and sufficient thickness to clean a cautery tip when the point of the cautery tip is plunged from the top surface well into the pad and withdrawn, said pad also having sufficient thickness to support a plurality of cautery tips in a point down, base up configuration when such tips are plunged into the pad and released;
   said base and said pad being constructed from materials suitable for sterilizing.

9. The cautery tip cleaner and holder of claim 8 in which said means for attaching the base to a surface comprises adhesive attached to the bottom surface of the base.

10. The cautery tip cleaner and holder of claim 8 in which said pad also contains a depression for holding surgical instruments in a generally horizontal orientation when not in use.

11. The cautery tip cleaner and holder of claim 8 in which said top surface of said pad additionally contains one or more elongated slits which penetrate the top surface of the pad and which have a first end, a second end, opposing abrasive walls and an abrasive floor for cleaning a cautery blade having two sides and an edge by pressing the edge of the blade down between any two opposing abrasive walls at the first end deforming the floor and compressing the pad to bring the opposing abrasive walls together against the sides of the cautery blade and then drawing the blade through the slit towards the second end to clean the cautery blade.

12. The apparatus of claim 8 in which said base is constructed from a hard plastic.

* * * * *